United States Patent [19]
Padilla et al.

[11] Patent Number: 5,984,895
[45] Date of Patent: Nov. 16, 1999

[54] VASCULAR BLOOD FLASHBACK CONTAINMENT DEVICE WITH IMPROVED SEALING CAPABILITY

[75] Inventors: William Padilla, Sandy; Arlin Dale Nelson, Midvale, both of Utah

[73] Assignee: Merit Medical Systems, Inc., South Jordan, Utah

[21] Appl. No.: 09/007,465

[22] Filed: Jan. 15, 1998

[51] Int. Cl.$^6$ ................................................ A61M 5/178
[52] U.S. Cl. .......................................... 604/168; 604/900
[58] Field of Search ................................. 604/168, 900, 604/164, 256

[56] References Cited

U.S. PATENT DOCUMENTS

| | | | |
|---|---|---|---|
| 4,020,835 | 5/1977 | Nordstrom et al. | 128/214.4 |
| 4,193,399 | 3/1980 | Robinson | 128/214.4 |
| 4,904,240 | 2/1990 | Hoover | 604/53 |
| 5,032,116 | 7/1991 | Peterson et al. | 604/168 |
| 5,066,284 | 11/1991 | Mersch et al. | 604/168 |
| 5,098,395 | 3/1992 | Fields | 604/168 |
| 5,108,375 | 4/1992 | Harrison et al. | 604/167 |
| 5,120,319 | 6/1992 | Van Heugten et al. | 604/168 |
| 5,135,488 | 8/1992 | Foote et al. | 604/97 |
| 5,242,414 | 9/1993 | Fischell et al. | 604/168 |
| 5,259,838 | 11/1993 | Taylor et al. | 604/97 |
| 5,295,969 | 3/1994 | Fischell et al. | 604/168 |
| 5,295,970 | 3/1994 | Clinton et al. | 604/168 |
| 5,449,344 | 9/1995 | Taylor et al. | 604/97 |
| 5,501,671 | 3/1996 | Rosen et al. | 604/168 |

Primary Examiner—John D. Yasko
Attorney, Agent, or Firm—Workman, Nydegger, Seeley

[57] ABSTRACT

A blood containment device for use with a vascular entry needle provides visual and tactile confirmation that a blood vessel has been properly entered. The device includes a blood visualization chamber defined by a compliant member which provides a visual indication that a needle connected to the device has accessed a selected blood vessel. The blood visualization chamber is vented to allow air to escape therefrom as it is displaced by blood entering the visualization chamber, while a gas permeable membrane in communication with the vent to prevent significant blood from escaping from the blood containment device. A sealing member formed on an outer surface at one end of the compliant member works in conjunction with the gas permeable membrane to prevent significant leakage of blood from the device. The compliant member pulsates with changes in blood pressure, thereby providing continuous tactile confirmation that the needle tip is properly positioned within the selected blood vessel. The device allows passage therethrough of an elongated medical instrument such as catheterization apparatus while preventing significant blood leakage from the device.

20 Claims, 12 Drawing Sheets

VASCULAR BLOOD FLASHBACK CONTAINMENT DEVICE WITH IMPROVED SEALING CAPABILITY

BACKGROUND OF THE INVENTION

1. The Field of the Invention

The present invention generally relates to vascular entry devices. More particularly, the invention relates to blood containment devices for use with a vascular entry needle to provide visual and tactile confirmation that the needle tip has entered into a blood vessel and to allow for the introduction of an elongated medical instrument through the device.

2. The Relevant Technology

It is a common medical procedure to insert a hollow needle into a patient's blood vessel for the purpose of either withdrawing blood or introducing a drug, guide wire, guide catheter, or the like into the blood vessel. One difficulty with such procedures, however, is determining when the tip of the needle is properly placed within the selected blood vessel. Another concern is that unless the blood is contained, vascular pressure, and arterial pressure in particular, can force a leakage or spray of blood through the needle which will escape through the opposite end of the needle. This can create a risk to medical personnel of exposure to blood-borne viruses, such as hepatitis and HIV, that may be present in the patient's blood.

The problems of blood containment and confirming proper needle placement are particularly applicable during the procedure for introducing a guide wire, catheter, or the like, into a patient's artery for carrying out procedures in or around the patient's heart. Such catheterization involves first creating access to the selected artery using a vascular entry needle of sufficient bore, and then inserting a guide wire, guide catheter, or other catheter apparatus through the needle and into the selected artery. Often, the guide wire is first inserted and located in a desired position, after which the catheter is inserted over the guide wire to the desired position. Self-guiding catheters may also be inserted without first using a guide wire. After the catheter apparatus has been placed into the desired position, the vascular entry needle can then be removed by sliding it backwards over and off the proximal end of the guide wire apparatus.

In performing a catheterization procedure, as noted above, it is crucial that the vascular entry needle be properly positioned within the selected blood vessel. When an ordinary entry needle is used, entry of the needle tip into the blood vessel is indicated by the escape of blood at the proximal end of the needle. However, this has the attendant contamination problems mentioned above.

Another problem is that, during positioning, the needle can be accidentally pulled out of the blood vessel or pushed through the opposite side of the vessel wall, which defeats the catheterization procedure. Accordingly, it is important after the needle tip first enters the blood vessel to confirm that the tip remains properly positioned within the blood vessel.

Various blood containment devices exist which are directed to solving the above problems. Two such devices are the AngioDynamics™ SOS Bloodless™ Entry Needle (U.S. Pat. No. 5,122,121) and the Arrow-Fischell EVAN™ Vascular Entry Needle. Both of these devices have a vascular entry needle attached to a transparent plastic containment member. The plastic containment member has a catheter guideway extending therethrough which allows insertion of catheterization apparatus through the device. The catheter guideway has a barrier within it which blocks blood from escaping, but allows passage of the catheterization apparatus.

Both devices also have features for indicating when the needle tip enters a blood vessel. The AngioDynamics™ SOS Bloodless™ Entry Needle has a length of transparent, flexible plastic tubing which branches off from the plastic containment member and leads to a small, collapsed, transparent plastic blood bag. When the needle tip is inserted into an artery, blood travels through the needle, into the guideway of the plastic containment member, out through the plastic tubing, and into the small blood bag. The soft plastic tubing of this device purportedly permits palpitation and visualization of the arterial pulse. However, the attached tube and blood bag can be cumbersome, particularly once the blood bag is filled. Also, once the blood bag is filled, the visual confirmation of needle tip placement stops.

The Arrow-Fischell EVAN™ Vascular Entry Needle provides for visualization of blood in a different way. The lower portion of the catheter guideway is narrow (about equal to the needle bore) for approximately two inches. It then opens into an air chamber near the upper portion of the device. When the tip of the vascular entry needle enters an artery, blood travels under pressure through the needle and partially fills the narrow lower portion of the guideway. It does this by slightly compressing the trapped air in the air chamber at the upper portion of the device. The thin column of blood then pulses back and forth in the guideway in response to the patient's heartbeat. This provides a visual indication that the needle tip is in a blood vessel. However, it can sometimes be difficult for a user of the device to see movement of the blood column, and there is no provision for tactile detection of the pulsating blood pressure.

Accordingly, there is a need for an improved device which allows for convenient visual and tactile confirmation of when an associated vascular entry needle enters a selected blood vessel, but which contains the blood to prevent its escape with the attendant contamination risks.

In addition, there is a need for a blood containment device that includes a flexible membrane that can fill with blood and provide visual and/or tactile confirmation of proper needle placement, which is configured to prevent or at least minimize leakage of blood while allowing for the venting of air therefrom.

Such blood containment devices having improved capability of preventing leakage of blood are disclosed and claimed herein.

SUMMARY OF THE INVENTION

The present invention is directed to a blood containment device for use with a vascular entry needle. The device includes a main body having proximal and distal openings with an internal guideway extending therebetween. The distal opening is adapted to communicatively connect to a vascular entry needle, and the proximal opening is adapted to receive an elongated medical instrument, such as a guide wire or catheter apparatus, for passage through the guideway and into the vascular entry needle.

A touch accessible compliant member or membrane is disposed in or around the main body portion and defines a blood containment visualization chamber that is in fluid communication with the distal opening of the device such that blood pressure at the distal opening is transmitted to the compliant member. This causes the compliant member to bulge and contract in response to increases and decreases, respectively, in blood pressure at the distal opening. The compliant member includes an end wall forming a barrier in the main body portion between the proximal and distal openings which prevents passage of blood out of the device through the guideway but which allows passage therethrough of an elongated medical instrument. The compliant member defines an interior space or volume into which blood flows, referred to as the blood visualization channel. The end wall of the compliant member has at least one vent opening that allows air to escape from the blood visualization chamber defined by the compliant member while blood is filling the chamber in order to allow blood to fill substantially the entire blood visualization chamber.

Preferably, the main body portion includes a rigid inner member with the guideway formed therethrough and a rigid outer member which fits around the compliant member and allows touch access to the compliant member through openings in the outer member. The rigid outer member has a dome-shaped proximal end that includes a guide fitting defining an insertion channel that is tapered in a funnel-like shape. The compliant membrane and the rigid outer member are adapted to receive an elongated medical instrument for passage through the guideway and the vascular entry needle.

A gas permeable member is preferably disposed between the end wall of the compliant member and the rigid outer member to allow air to escape from the device while preventing the passage of blood out of the device. Additionally, a support member such as a flange can be disposed internally between the compliant member and the rigid inner member to prevent over-squeezing or excess depression of the compliant member.

A sealing member can be formed on an outer surface of the end wall of the compliant member to enhance blood leakage prevention. The sealing member works in conjunction with the gas permeable member to prevent leakage of blood from the device. In one preferred embodiment, the sealing member includes concentric inner and outer circular ridges defining a blood collecting channel therebetween. The vent opening in the compliant member is in communication with the blood collecting channel such that blood passing through the vent opening will fill the blood collecting channel and contact the gas permeable member. In addition, the guide fitting in the rigid outer member can include a continuous interior ridge that cooperates with the sealing member to enhance blood leakage prevention. For example, the continuous interior ridge can abut against the inner circular ridge of the sealing member to provide a more secure seal.

Upon insertion of a needle attached to the blood containment device into a blood vessel, blood flows through the needle and into the blood visualization chamber defined by the compliant member, thereby providing a visual indication that the blood vessel has been properly entered. As blood enters the blood visualization channel, air is forced out the vent hole and through the gas permeable membrane, thereby allowing blood to substantially completely fill the visualization channel or chamber. The gas permeable membrane becomes sealed upon being wetted with blood such that blood is contained within the containment device. When the visualization chamber is substantially filled, blood pressure causes the compliant member to bulge or pulsate in and out, which can be detected both visually and tactically by a user holding the device, thereby providing an indication that the vascular needle tip has been properly positioned in the selected blood vessel. With proper needle placement, the compliant member of the device will continue to pulsate with the patient's heartbeat, providing continuing confirmation of proper needle placement.

The blood containment device of the invention can be used in initiating catheterization procedures while minimizing exposure to a patient's blood by providing for blood containment during vascular access. After accessing a blood vessel, the device allows for placement of a medical instrument such as a guide wire therethrough for subsequent catheterization procedures.

Accordingly, a principal object of the present invention is to provide a device which allows for convenient visual and tactile confirmation of when an associated vascular entry needle has been properly placed within a selected blood vessel.

Another object of the invention is to provide a device which contains or substantially prevents leakage of blood after vascular entry by a needle to prevent escape of the blood with the attendant contamination risks.

A further object of the invention is to provide a device that allows an elongated medical instrument to be inserted therethrough while the device contains blood from an accessed blood vessel.

Yet another object is to provide a compliant membrane that includes an improved sealing mechanism or features which substantially prevent leakage of blood from the compliant membrane, particularly in the region of the vent hole and gas permeable membrane.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

Figure 1:
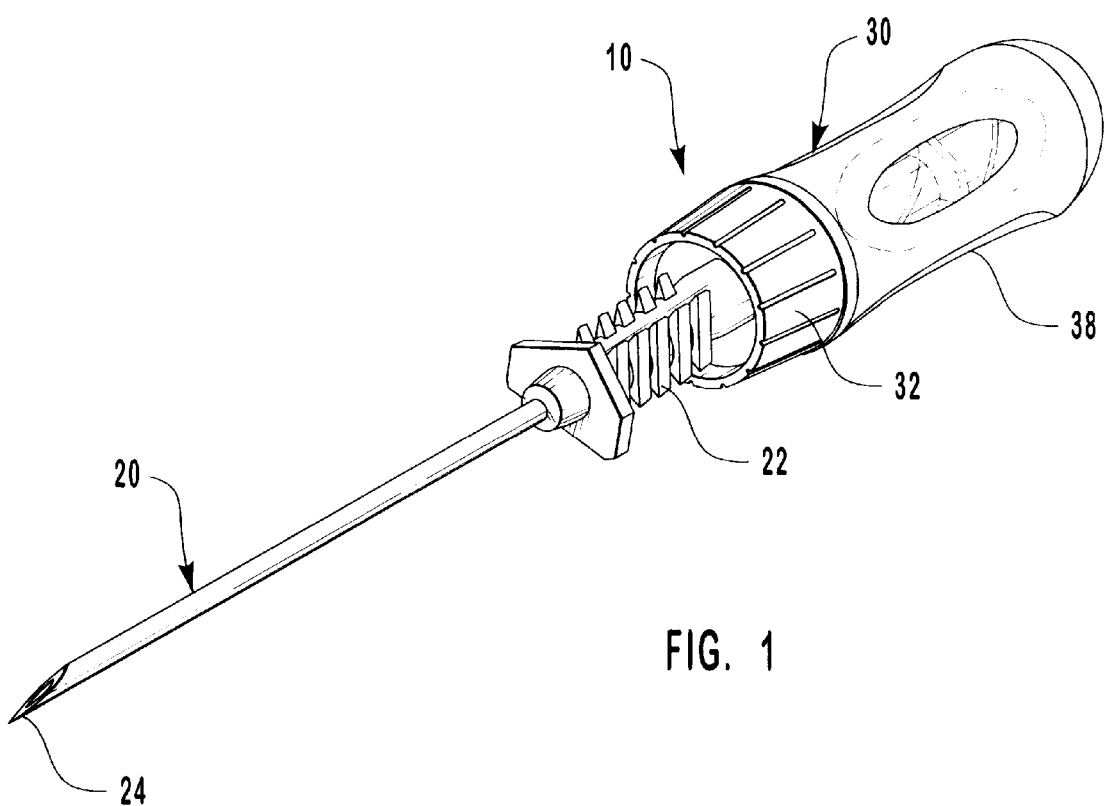
FIG. 1 is a perspective view of the blood containment device according to the invention coupled to a vascular entry needle.

The present invention is directed to a blood containment device for use with a vascular entry needle which provides visual and tactile confirmation that a blood vessel has been properly entered by the needle. A visualization chamber defined by a compliant member indicates whether the needle connected to the device has entered the selected blood vessel. The compliant member pulses with changes in blood pressure, thereby providing a tactile indication that the needle tip is properly positioned in the blood vessel. The device allows passage therethrough of an elongated medical instrument such as catheterization apparatus while preventing blood leakage from the device. The device of the invention can, thus be used to initiate catheterization procedures while minimizing exposure to a patient's blood by providing for blood containment during vascular access.

Referring to the drawings, wherein like structures are provided with like reference designations, the blood containment device according to the invention is depicted in alternative embodiments.

FIG. 1 shows an assembled blood containment device according to the invention that has been coupled to a vascular entry needle to form a vascular access device 10. As shown, the vascular access device 10 includes a vascular entry needle 20 coupled to one embodiment of a blood containment device 30. The needle 20 includes a proximal coupling section 22 adapted to removably attach to a main body portion of the blood containment device 30 such as through a luer lock connection. A distal needle tip 24 is adapted to penetrate a blood vessel during a medical procedure. A rigid inner member 32 interconnects with a rigid outer member 38, as discussed in further detail below, to form an outer housing for the blood containment device 30. During use, the vascular access device 10 provides visual and tactile indication of proper needle placement in a blood vessel.

This embodiment of the blood containment device 30 is shown in further detail in FIGS. 2–8. The blood containment device 30 corresponds substantially with one of the preferred embodiments disclosed in copending U.S. application Ser. No. 620,922, filed on Mar. 22, 1996, the disclosure of which is incorporated herein by reference.

Figure 2:
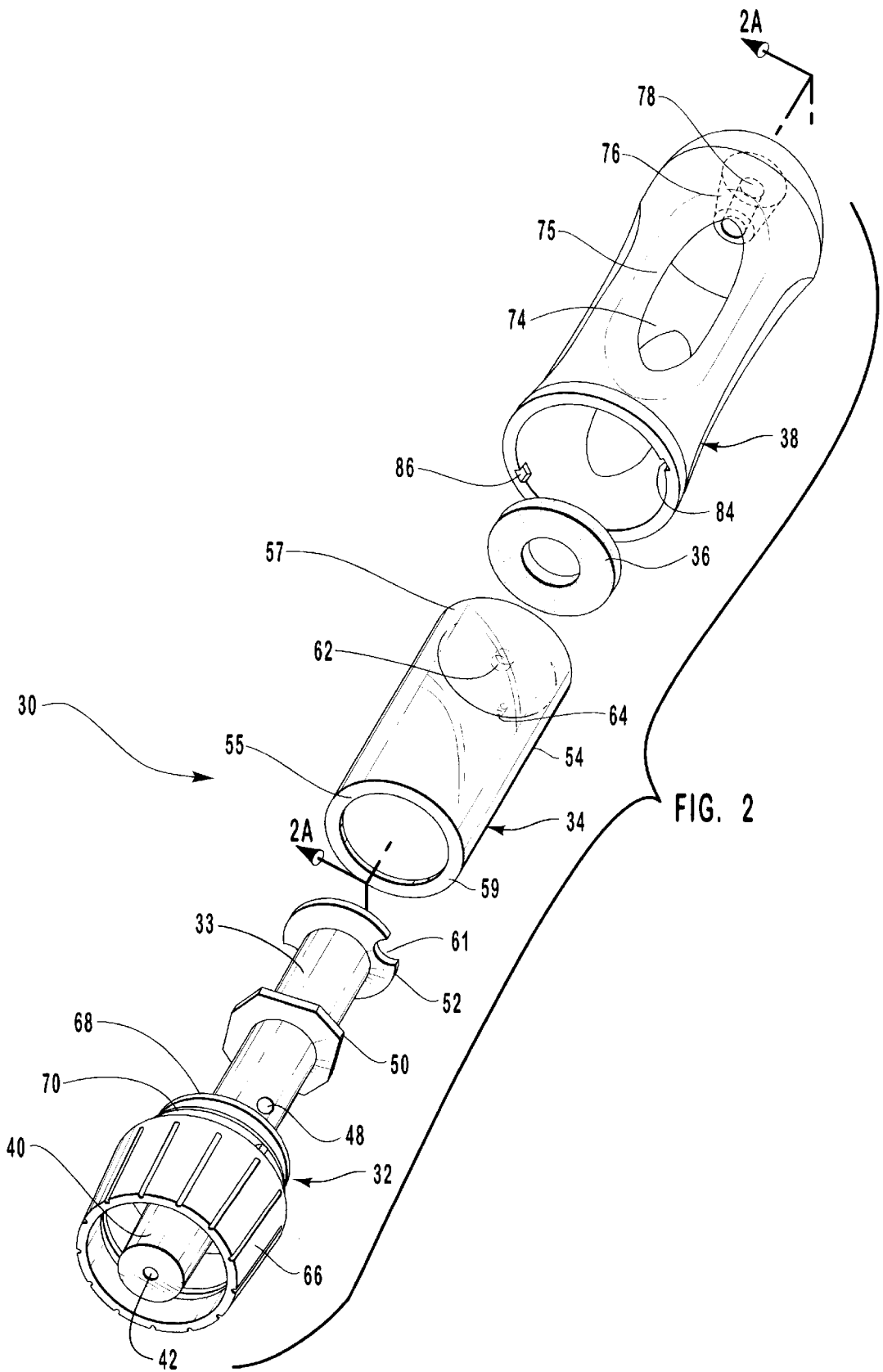
FIG. 2 is a perspective exploded view of one embodiment of the blood containment device of the invention.
Figure 2A:
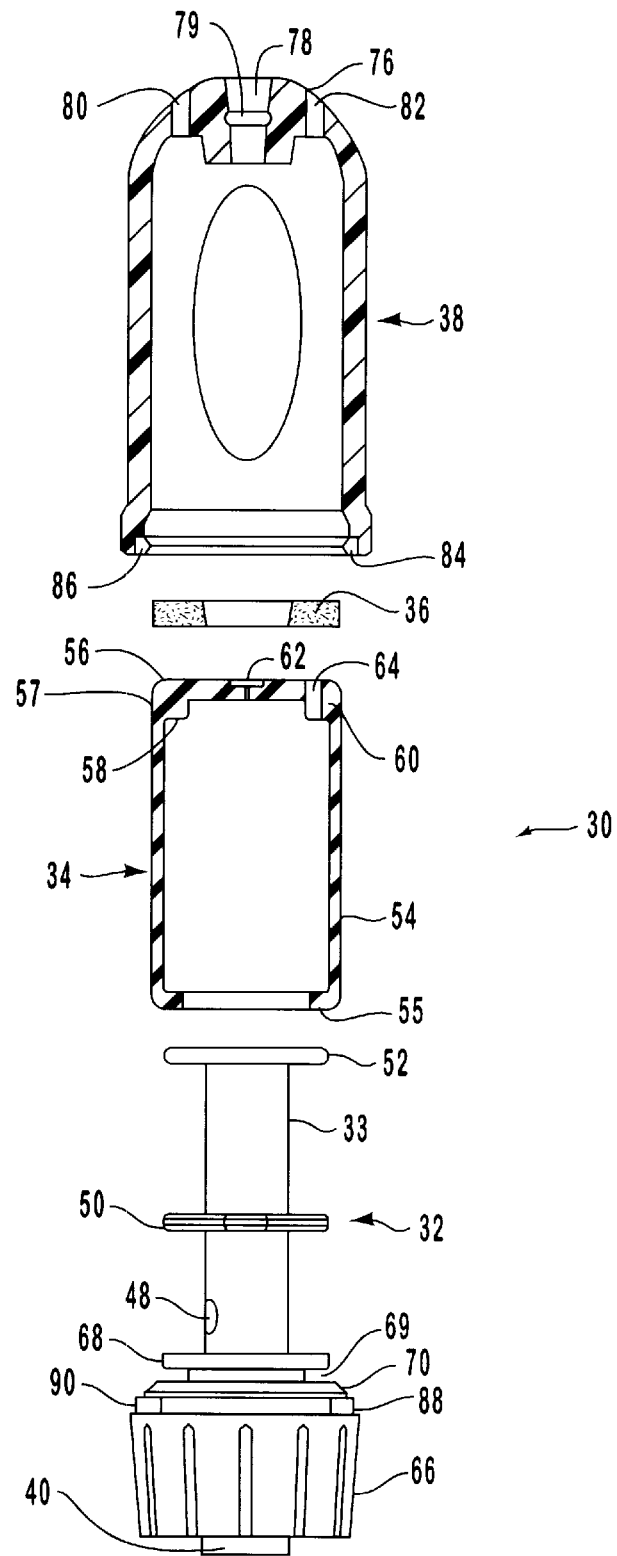
FIG. 2A is a cross-sectional exploded view of the embodiment shown in FIG. 2.
Figure 3:
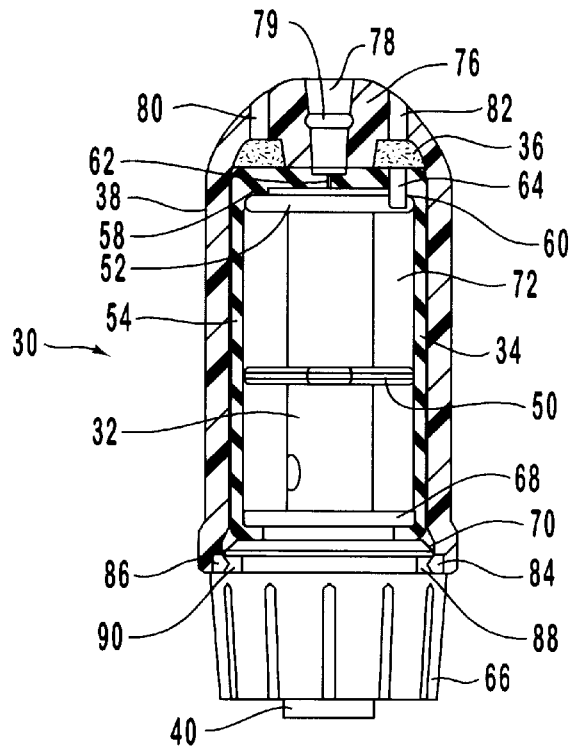
FIG. 3 is an assembled cross-sectional view of the embodiment shown in FIG. 2A.

As best seen in FIGS. 2, 2A and 3, the blood containment device 30 generally includes a rigid inner member 32, a compliant member or membrane 34, and a rigid outer member or shell 38, which form the main body portion of device 30. A gas permeable member or ring 36 is disposed in the main body portion of device 30. The compliant membrane 34 and the outer shell 38 are preferably transparent to allow for visualization of blood passing into containment device 30. When assembled, the compliant membrane 34 overfits a portion of the rigid inner member 32, and the outer shell 38 overfits the compliant membrane 34, with the gas permeable ring 36 interposed between the compliant membrane 34 and the outer shell 38. Each of the above components will be discussed below in further detail.

As shown in FIGS. 2–5, the rigid inner member 32 has a cylindrical section 33 and a connector section 66. The connector section 66 preferably includes a male luer lock fitting 40 having a male luer terminating in a distal opening 42 for connection to a standard female luer connection, such as at the proximal coupling section 22 of the vascular entry needle 20. A guideway 44, as shown in cross-sectional view in FIG. 5, extends from the distal opening 42 of the male luer lock fitting 40 to a proximal opening 46 of the rigid inner member 32. The proximal opening 46 provides access for a guide wire, J-Straightener, or other medical instrument. At least one, and preferably two, blood communication ports 48 extend between the guideway 44 and the exterior of the rigid inner member 32. Preferably, the rigid inner member 32 is made of a material such as ABS (acrylonitrile butadiene styrene) or other suitable type of rigid plastic.

Figure 4:
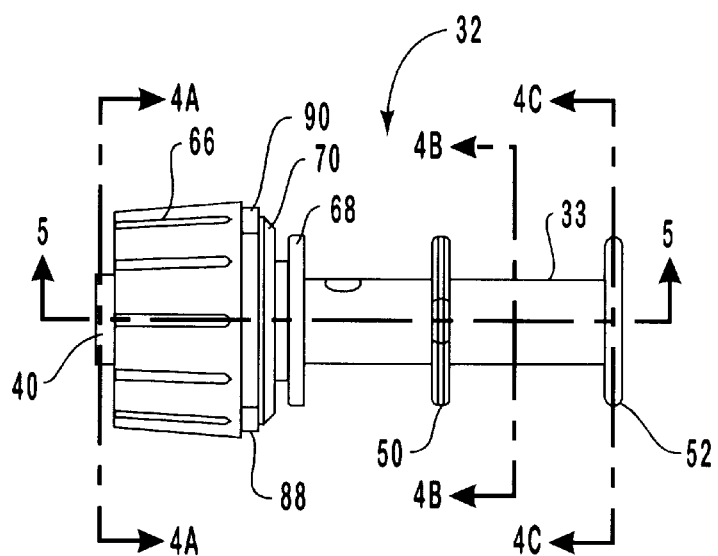
FIG. 4 is a side view of the rigid inner member employed in the embodiment shown in FIG. 2.
Figure 4A:
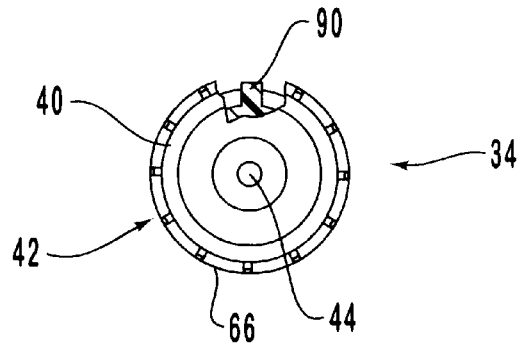
FIGS. 4A–4C are cross sectional views taken along lines 4A—4A, 4B—4B, and 4C—4C, respectively, of FIG. 4, with a cut away portion in FIG. 4A.
Figure 4B:
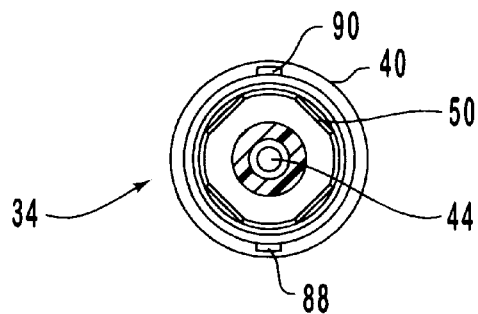

To prevent excess flexure or depression of the compliant membrane 34, an inner support member may be provided in the blood containment device. The optional inner support member is spaced from the inside surface of the compliant member to permit tactile confirmation, by slight depression of the compliant membrane, of proper needle placement, but prevents excessive depression or over-squeezing of the compliant membrane. In the illustrated embodiment of FIGS. 2–5, the rigid inner member 32 includes such an inner support member in the form of a flange or ring 50 located between the blood communication ports 48 and the proximal opening 46. Although shown as a single flange or ring, multiple flanges or rings or other structures such as raised axial ribs, columns or the like could be used as the inner support member. Preferably, as shown in FIGS. 2 and 4B, the flange 50 is square and has rounded corners, although other shapes may be chosen without departing from the invention. The rectangular flange 50 limits the amount the compliant membrane 34 can be squeezed in order to limit the reduction of the inner volume of the membrane 34 from manual tactile pressure by the user, thereby preventing excess depression of the membrane 34, which might cause excessive backflow of blood back into the person's blood vessel.

Figure 4C:
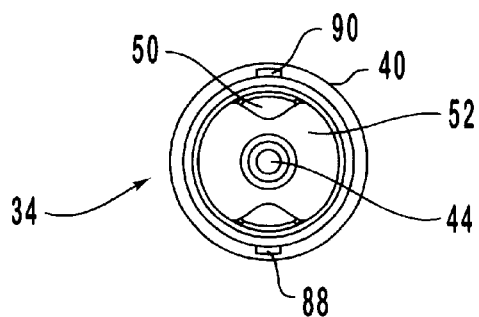
Figure 5:
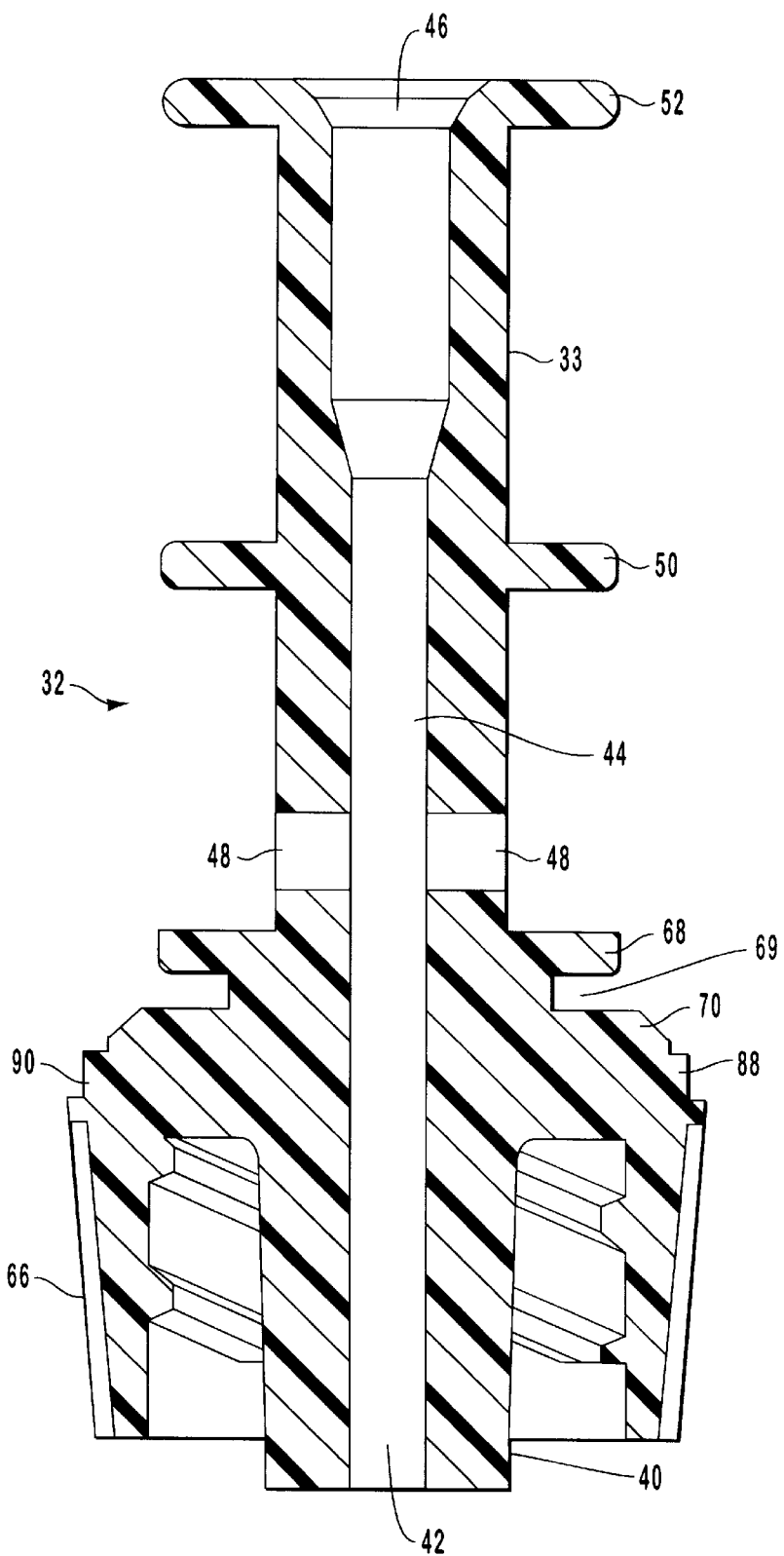
FIG. 5 is a longitudinal cross-sectional view of the rigid inner member of FIG. 4, taken along line 5—5 of FIG. 4.

To engage and rest against one end of the compliant membrane 34, an annular flange or rest 52 is provided around the proximal opening 46 of rigid inner member 32. Preferably, as shown in FIGS. 2 and 4C, the annular flange 52 has two opposing semi-circular cut outs 61, the purpose of which will be more fully explained hereafter.

FIGS. 2, 3, 6 and 7 comprise different views of the compliant member or membrane 34. The compliant membrane 34, as shown in cross-sectional view in FIGS. 2A, 3, 6 and 7, has a circumferential side wall 54 forming a hollow cylindrical shape which terminates at a distal end 55 and a proximal end 57. The distal end 55 of the membrane 34 is open, and the proximal end 57 is substantially closed by an end wall 56. The compliant membrane 34 is preferably made of a compliant elastomeric or flexible material, such as a thermoplastic elastomer sold under the trademark "C-Flex" by CPT (Consolidated Polymeric Technologies, Inc.), silicone rubber, urethane, Mylar, Nylon, PEBAX, or any other material that will form a compliant membrane wall which will move sufficiently in response to blood pressure within the device for tactile sensation. In the preferred embodiment, "C-Flex" is used. It is believed that the chemical composition of "C-Flex" is a styrene-ethylene/butylene-styrene block copolymer with polydimethylsiloxane, polypropylene, USP grade mineral oil, antioxidant and other modifiers. The amount of movement of the membrane wall is a function of the material used, the wall thickness, and the area of the circumferential side wall 54 against which the blood pressure acts.

Figure 6:
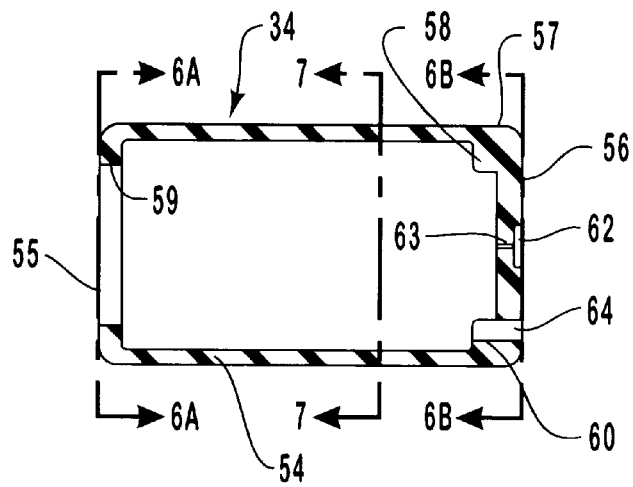
FIG. 6 is a longitudinal cross-sectional view of the compliant membrane employed in the embodiment shown in FIG. 2.
Figure 6A:
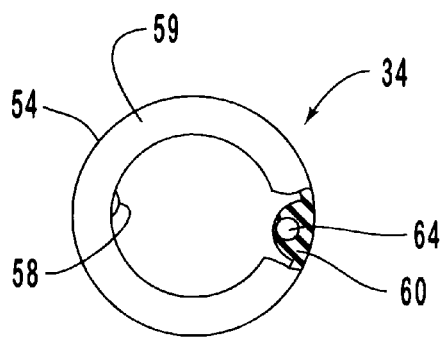
FIGS. 6A–6B are end views of the compliant membrane of FIG. 6 taken along lines 6A—6A and 6B—6B, respectively, with a portion of FIG. 6A removed.

As best seen in FIGS. 6 and 6A, two semi-circular formations 58, 60, are provided along the inner surface of the compliant membrane 34 at the proximal end 57. The semi-circular formations 58, 60 fit within the semi-circular cut-outs 61 in the annular flange 52 of the rigid inner member 32 (shown in FIGS. 2 and 4C), and the interior surface of the end wall 56 of the compliant membrane 34 rests against the annular flange 52 when the blood containment device 30 is properly assembled (see FIG. 3). The alignment of the semi-circular formations 58, 60 with the annular flange 52 helps to stabilize the relative motion between the rigid inner member 32 and the compliant membrane 34.

Figure 6B:
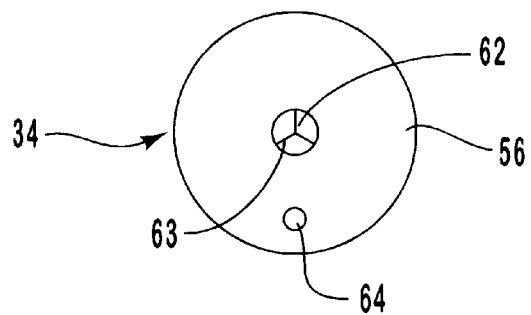

As shown in FIGS. 6 and 6B, the end wall 56 of the compliant membrane 34 has a shallow hollow depression 62 that does not completely penetrate the end wall. Preferably, the area below the depression 62 is perforated with a tricuspid punch to produce a valve slit 63 that will allow the passage of an elongated medical instrument such as a guide wire but will not allow the passage of significant quantities of blood therethrough. The valve slit 63 is normally closed to prevent significant blood from traveling through end wall 56. When an elongated medical instrument is inserted in the device 10, the valve slit 63 facilitates penetration of the instrument through the end wall 56 of compliant membrane 34, while substantially sealing around the instrument to prevent significant blood from escaping past the end wall 56.

The end wall 56 and the semi-circular formation 60 of the compliant membrane 34 includes a perforation, as shown in FIGS. 6 and 6A, which creates a vent opening 64. The vent opening 64 is aligned with one of the semi-circular cut-outs 61 in the annular flange 52 of rigid inner member 32, and allows air to escape from the interior of the compliant membrane 34 to the exterior of the membrane 34. In a preferred embodiment, the compliant membrane includes only a single vent opening. However, multiple vent openings can be used, with the size and number of vent openings determining how fast the blood will fill up the membrane. For example, the end wall 56 and the semi-circular formation 58 may also be perforated to create a second vent opening. With a second vent opening, air will escape the device more quickly, which, in turn, allows the membrane to fill up more quickly with blood.

Figure 7:
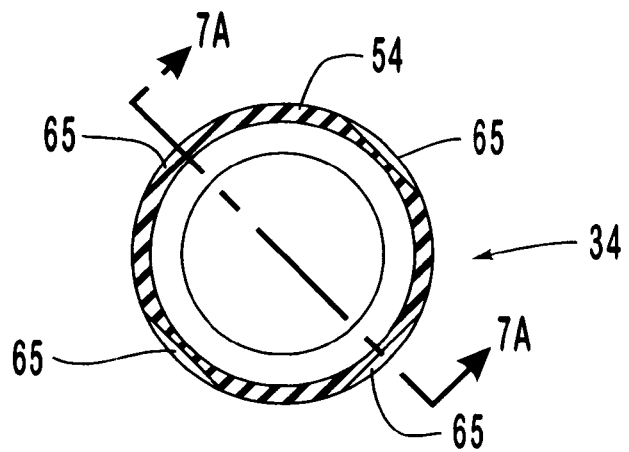
FIG. 7 is a transverse cross-sectional view of the compliant membrane of FIG. 6, taken along line 7—7 of FIG. 6.
Figure 7A:
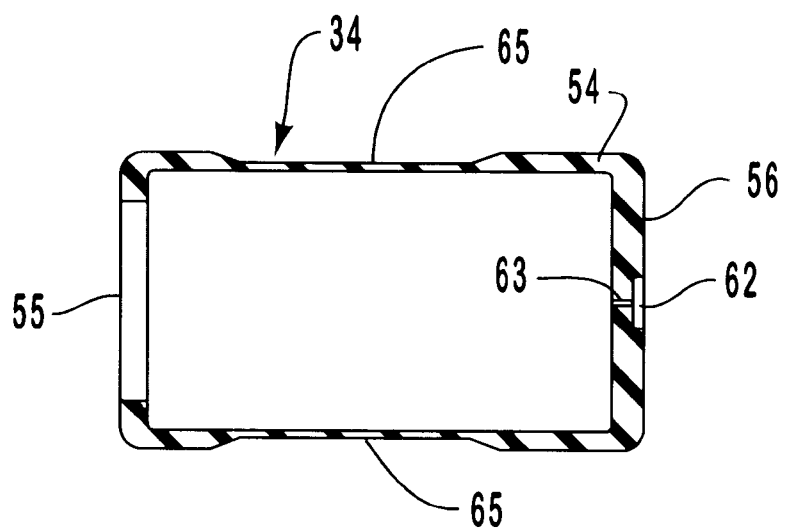
FIG. 7A is a longitudinal cross-sectional view of the compliant membrane of FIG. 7, taken along line 7A—7A of FIG. 7.

The exterior surface of the circumferential wall 54 of the compliant membrane 34 preferably includes a plurality of tactile enhancing areas 65, such as elongated areas of reduced thickness as shown in FIGS. 7 and 7A, or raised dimples, ribs, or the like. The areas of reduced thickness provide greater movement in response to changes in blood pressure within the device than areas of unreduced thickness in the compliant membrane 34. Other tactile enhancing features, such as bumps, dents, crenelations, and the like, that facilitate tactile sensation of the compliant membrane wall as it moves, and which may also enhance visual feedback of blood flow, can also be used. For example, dimples formed on the circumferential side wall 54 could be formed with a thinner wall thickness than the surrounding wall in order to provide greater movement of the dimples under blood pressure. As illustrated, there are four tactile enhancing areas 65 located around the compliant membrane 34.

As shown in FIGS. 2A and 3, the compliant membrane 34 fits over a proximal portion of the rigid inner member 32 adjacent to the connector section 66. To provide a sealing groove for interfitting with the distal end 55 of the membrane 34, the rigid inner member 32 includes two spaced annular ribs or ridges 68, 70, which define a sealing groove 69 therebetween. The distal end 55 of the compliant membrane 34 includes an annular inner ring 59, as best seen in FIGS. 2 and 6A, that is received into the sealing groove 69 on the rigid inner member 32. If desired, a bonding cement, adhesive or other suitable mechanical connection may be used to attach and seal the compliant membrane 34 to the rigid inner member 32 along the sealing groove 69. As a result of this connection between the compliant membrane 34 and the rigid inner member 32, an internal visualization chamber 72 is defined therebetween, as best seen in FIG. 3.

When the compliant membrane 34 is placed over the rigid inner member 32, the rectangular flange 50 is typically at about the mid-point between the proximal end wall 56 and the distal end 55 of the membrane 34 (see FIG. 3). Having the flange 50 at this point is intended to limit the amount the compliant membrane 34 can be squeezed or depressed, and thereby limit the amount the inner volume of the membrane can be reduced. If the flange is not used, excess pressure can be applied to the side walls of the membrane, forcing blood and/or air back through the needle.

The gas permeable ring 36 is located adjacent to the outer surface of the end wall 56 of the compliant membrane 34 (see FIGS. 2–3) and is disposed over the vent opening(s) 64 to allow air to vent from the chamber 72, while preventing significant passage of blood therethrough. The gas permeable ring 36 is preferably made of a hydrophobic material that allows for the passage of gas but not liquid. Alternatively, the material may be self-sealing upon contact with blood. Such a self-sealing material immediately seals upon contact with the liquid (i.e., blood). Once the material has sealed, air as well as blood or any other liquid cannot pass through the ring. Preferably, the ring is manufactured from porous polyethylene, which is available from Porex Technologies Corporation.

The gas permeable ring 36 allows air within the blood containment device to escape through the vent opening 64 as the patient's blood fills the device. This air within the device is allowed to escape up until the time when there is contact between the patient's blood and the gas permeable ring 36. When the ring 36 is made of a self-sealing material, the blood is contained as it continues to pulse within chamber 72, with the ring 36 initially allowing the passage of air, but preventing the passage of significant amounts of blood outside the vent opening 64.

Alternatively, the gas permeable material may be in the form of a self-sealing gas permeable filter rod (not shown)

disposed within each vent opening(s). As the self-sealing gas permeable rod(s) would be made of the same material described above for the gas permeable ring, the rod(s) would also initially allow the passage of air from the vent opening. Then, once blood contacts the rod(s), they would prevent the passage of air or blood. The rod(s) could be used independently or in combination with the gas permeable ring.

Figure 8:
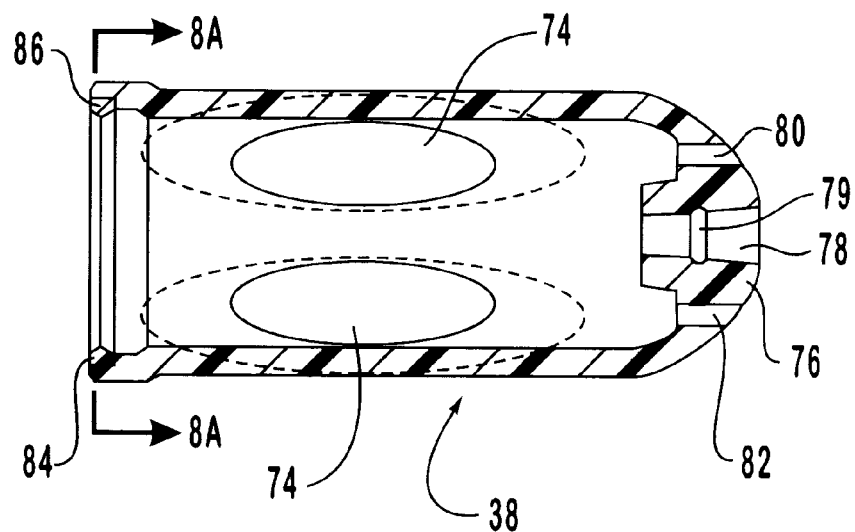
FIG. 8 is a longitudinal cross-sectional view of the rigid outer member employed in the embodiment shown in FIG. 2.

The rigid outer member 38, shown in FIGS. 2–3 and 8, has a generally hollow cylindrical shape with a dome-shaped top. Preferably, the rigid outer member 38 is made of a relatively rigid transparent plastic material, such as for example K-resin or ABS. As shown in FIGS. 2A and 3, the rigid outer member 38 fits over the compliant membrane 34, and is attached to the rigid inner member 32 at the annular ridge 70 with bonding cement, adhesive, a weld, or a mechanical connection. This forms an outer support housing and helps to secure the compliant membrane 34 in place.

As best seen in FIGS. 2 and 8, a plurality of large oval side openings 74 are located around the circumference of the rigid outer member 38, preferably corresponding with and surrounding the tactile enhancing areas 65 of the compliant membrane 34. Preferably, four such side openings are located on the outer member 38. Each oval side opening 74 is preferably surrounded by a slightly curved, oval area or ring 75 that provides a natural rest for a user's fingertip. The curved, oval area 75 is preferably slightly sloped from its outer to inner diameter. The openings 74 are aligned with and preferably larger than the elongated areas of reduced thickness or raised dimples or other tactile-enhancing features of the compliant membrane 34, and provide touch access by a user of the device to the exterior surface of the compliant membrane 34. The elongated areas of reduced thickness or raised dimples are preferably sized to protrude out slightly beyond the rigid outer member 38 when the elongated areas or raised dimples are under substantial pressure from the pumping of blood filling the blood visualization channel 72.

A cone-shaped guide fitting 76, shown in FIGS. 2–3 and 8, is located at the proximal end of the device 30. As best seen in FIGS. 2A, 3, and 8, the guide fitting 76 is formed in the dome-shaped top of the rigid outer member 38. An insertion channel 78 extends through the guide fitting 76 and extends slightly beyond the top interior surface of the rigid outer member 38. The guide fitting 76 facilitates initial entry of a J-tipped elongated medical instrument into the device such as the many different types of "J-Straighteners" that are commercially available. The insertion channel 78 may be adapted so that any of the existing J-Straighteners can lock thereinto. Preferably, the insertion channel 78 is tapered in a funnel-like shape and includes an annular snap groove 79 that allows a modified J-Straightener (not shown) to lock into the guide fitting 76 of the blood containment device when the modified J-Straightener is inserted. The J-Straightener can be modified to have a mate for the snap groove, such as an exterior ring.

As shown in FIG. 3, the gas permeable ring 36 fits around an extended portion of the guide fitting 76 in the interior of the rigid outer member 38. The rigid outer member 38 may have only one vent hole or may have two or more vent holes. FIGS. 2A, 3 and 8 show two vent holes 80, 82 in the rigid outer member 38. The gas permeable ring 36 is aligned with the two vent holes 80, 82 located in the rigid outer member 38 and the vent hole 64 in the compliant membrane 34 so as to allow air to be vented to the outside while preventing the passage of significant blood to the outside of the blood containment device.

Figure 8A:
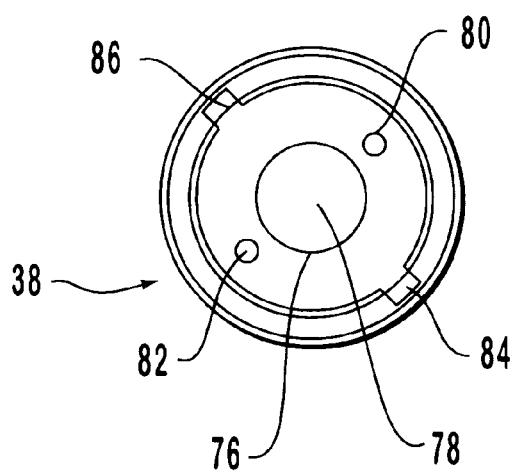
FIG. 8A is an end view of the rigid outer member of FIG. 8, taken along line 8A—8A of FIG. 8.

For proper orientation of the various parts of the device, the distal end of the rigid outer member 38 preferably includes two opposing, hollow rectangular cut-out areas 84, 86, as shown in FIGS. 8 and 8A. The cut-out areas 84, 86 are intended to fit over two opposing rectangular orientation tabs 88, 90 (shown in FIGS. 2A, 4 and 5) on the connector section 66 of the rigid inner member 32. FIG. 4A has a portion cut away to show the orientation tab 90. As shown in FIG. 3, the orientation tabs cooperate with the cut-out areas 84, 86 to provide guidance when assembling the blood containment device and placing the rigid outer member 38 over the compliant membrane 34. Preferably, the orientation tabs 88, 90 and the cut-out areas 84, 86 snap-fit together so as to secure the rigid outer member 38 to the rigid inner member 32 in a desired orientation.

The blood containment device of the invention can be used in initiating catheterization procedures while minimizing exposure to a patient's blood by providing for blood containment during vascular access. Upon accessing a blood vessel, the device provides visualization of blood flashback as well as containment of blood.

For example, in using the blood containment device shown in FIGS. 1–5, the needle tip 24 of the vascular entry needle 20 punctures a selected blood vessel, with blood passing through the needle shaft and through the distal opening 42 of the luer lock fitting 40. The blood then flows through the guideway 44 and the blood communication port(s) 48 into visualization chamber 72 defined between the compliant membrane 34 and the rigid inner member 32, as best seen in FIG. 3. This provides an immediate visual indication that the needle tip 24 has entered a blood vessel.

With the next few pulses of blood, the chamber 72 becomes filled, providing a further visual indication that the needle tip 24 remains properly positioned within the selected blood vessel. As blood fills the device, air is displaced and passes through the vent opening 64, through the gas permeable ring 36, and through one of the vent holes 80 or 82 until blood contacts the ring 36. At that point, the gas permeable ring 36 preferably self-seals so that blood is not allowed to escape and is contained within the device, while air is prevented from entering therein, thereby reducing the risk of contamination. When the device becomes filled with blood and the blood is blocked by the gas permeable ring 36, blood pressure causes the compliant membrane 34 to bulge and then pulsate with the patient's heartbeat. This provides a user of the device with an ongoing tactile confirmation that the attached needle tip remains properly situated within the selected blood vessel, since the membrane 34 pulsates due to the pulsating blood pressure from the patient's heartbeat.

Once the vascular entry needle 20 is properly positioned and stabilized, an elongated medical instrument or catheterization apparatus, such as a guide wire or catheter of typical construction (not shown), is carefully advanced through the device into the blood vessel as far as required for subsequent catheterization procedures. For example, a guide wire can be introduced into insertion channel 78 of rigid outer member 38 and pushed through valve slit 63. The guide wire is then maneuvered along guideway 44 and through the vascular entry needle 20 into the selected blood vessel until the desired position is reached. The blood containment device 30 and the attached needle 20 are then removed by sliding these back over and off the guide wire, leaving the guide wire in place in the blood vessel. The guide wire is then used as required for further catheterization procedures.

Another preferred embodiment of the invention is shown in FIGS. 9–12 in the form of a blood containment device 130, which includes substantially the same components and operates in the same manner as the blood containment device 30 shown in FIG. 2. Thus, the blood containment device 130 generally includes a rigid inner member 132, a compliant member or membrane 134, a gas permeable member or ring 136, and a rigid outer member or shell 138. These components function in the same manner as the corresponding components described above for the containment device 30, and thus will not be discussed in further detail except as necessary to describe additional features in the containment device 130. In addition, the procedures for inserting and positioning an elongated medical instrument, such as catheterization apparatus, through the containment device 130 is the same as described above in connection with the containment device 30.

The blood containment device 130 adds additional features to the compliant membrane 134 and to the rigid outer member 138 to provide enhanced sealing characteristics for the device 130. In particular, the blood containment device includes an improved venting system which allows passage of air from within the blood visualization channel, but which includes an improved sealing mechanism to substantially prevent leakage of blood through the venting system.

Figure 10:
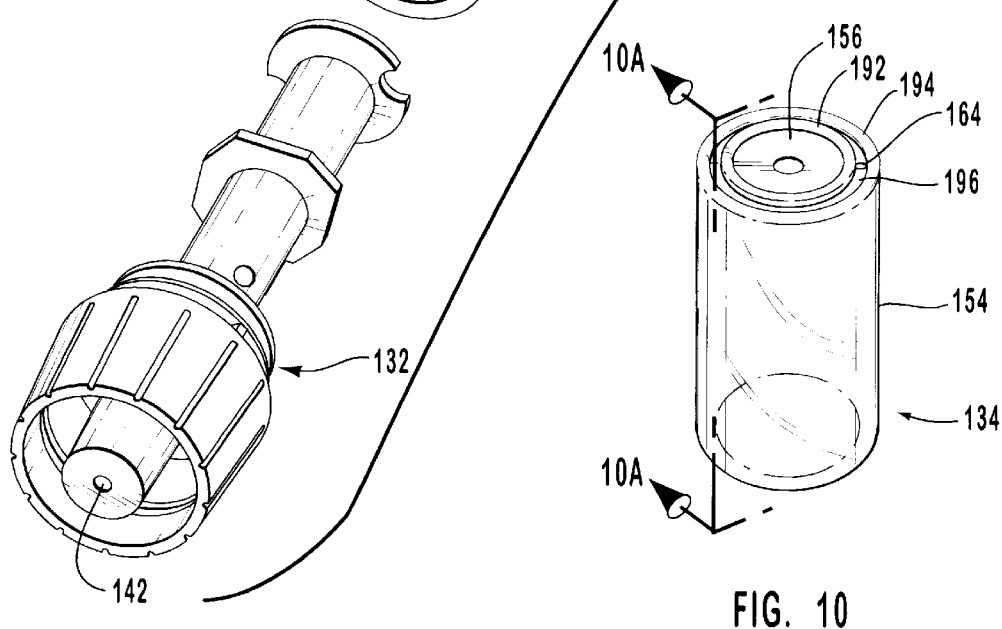
FIG. 10 is a perspective view of the compliant membrane employed in the embodiment shown in FIG. 9.
Figure 10A:
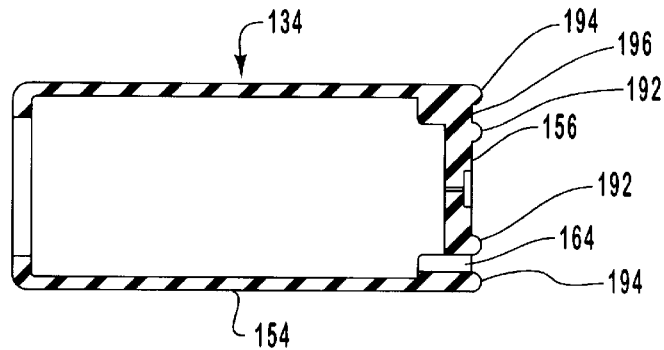
FIG. 10A is a longitudinal cross-sectional view of the compliant membrane of FIG. 10, taken along line 10A—10A of FIG. 10.
Figure 11:
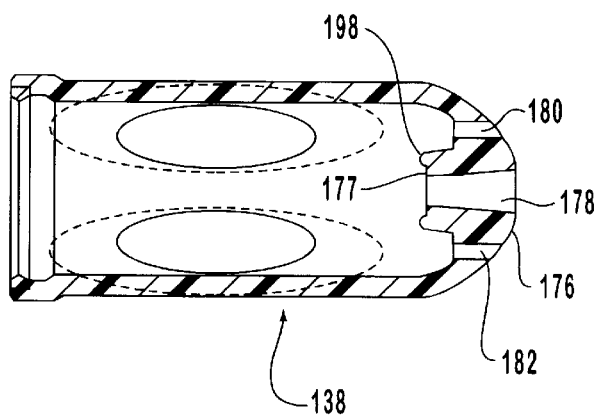
FIG. 11 is a longitudinal cross-sectional view of the rigid outer member employed in the embodiment shown in FIG. 9.

As depicted in FIGS. 10 and 10A, the compliant membrane 134 includes a side wall 154 and an end wall 156. A sealing means for enhancing the sealing characteristics of the device 130 to prevent leakage of fluid such as blood is provided on the top surface of the compliant membrane 134. The sealing means works in conjunction with the gas permeable member 136 to prevent leakage of blood from the device. A presently preferred embodiment of the sealing means includes a sealing member formed on an outer surface of the end wall 156 of the compliant membrane 134 to enhance blood leakage prevention. The sealing member includes two continuous concentric ridges, including a circular inner ridge 192 and a circular outer ridge 194, which are formed on the outer surface of the end wall 156. As shown in FIG. 10A, the inner ridge 192 and the outer ridge 194 have a semi-circular cross-sectional shape.

The inner ridge 192 and the outer ridge 194 define a circular blood collecting channel 196 therebetween. A vent opening 164 in the end wall 156 is interposed between the inner and outer ridges 192, 194. The vent opening 164 provides fluid communication between the blood collecting channel 196 and an internal visualization chamber 172 defined by the compliant membrane 134 and the rigid inner member 132. Blood passing through the vent opening 164 will thus fill the blood collecting channel 196 and contact the gas permeable member 136. The inner and outer ridges 192, 194 form continuous seats on the end wall 156 of the compliant membrane 134 and provide enhanced sealing characteristics to prevent leakage of blood from the containment device 134.

As illustrated in FIG. 1, the rigid outer member 138 includes a guide fitting 176 formed in the dome-shaped top of the outer rigid member 138. The guide fitting 176 defines an insertion channel 178 extending therethrough that is adapted to receive an elongated medical instrument such as a guide wire. A pair of vent holes 180 and 182 are formed through the dome-shaped top of the rigid outer member 138 and are adjacent to the guide fitting 176. A continuous circular interior ridge 198 is formed on an inner surface 177 of the guide fitting 176 where the insertion channel 178 terminates. The interior ridge 198 has a semi-circular cross-sectional shape. The interior ridge 198 cooperates with the sealing member on the compliant member 134 to enhance blood leakage prevention in the device.

Figure 9:
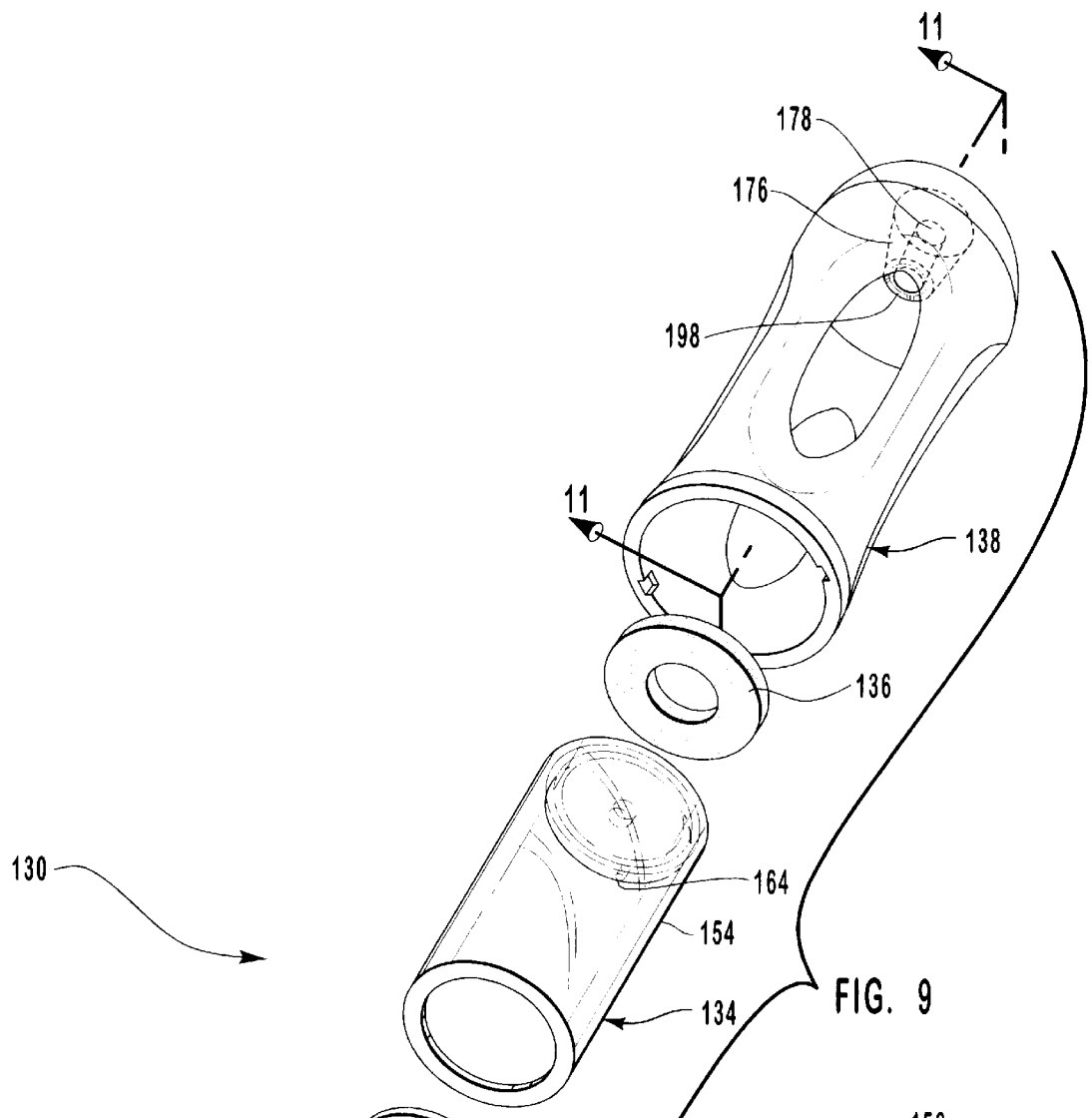
FIG. 9 is a perspective exploded view of another embodiment of the blood containment device of the invention.
Figure 12:
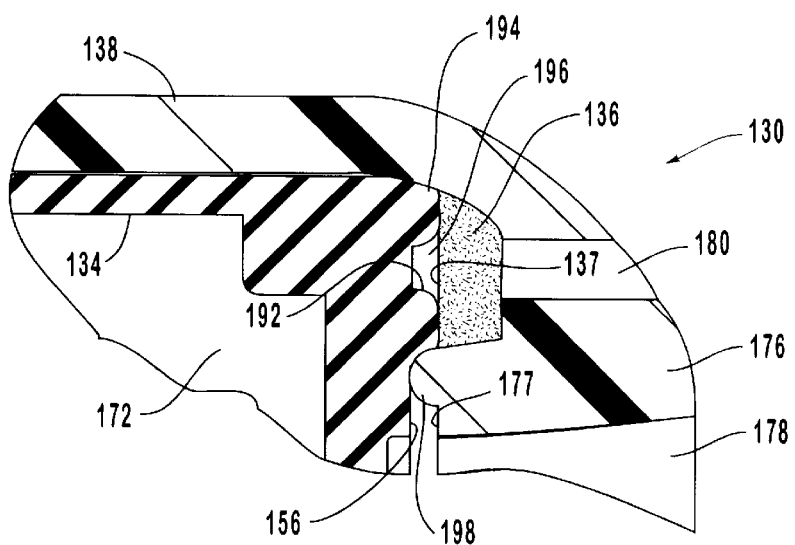
FIG. 12 is an enlarged partial cross-sectional view of the blood containment device of FIG. 9 shown in an assembled condition.

FIG. 12 is an enlarged partial cross-sectional view of the containment device 130 in an assembled condition showing in greater detail the sealing features of the embodiment of FIG. 9. As shown in FIG. 12, the gas permeable ring 136 is disposed between the rigid outer member 138 and the end wall 156 of the compliant membrane 134. Portions of an inner surface 137 of the gas permeable ring 136 abut against the softer inner and outer ridges 192, 194 on the compliant membrane 134, such that the inner and outer ridges 192, 194 are slightly deformed against the inner surface 137 of the gas permeable ring 136. This creates a tight seal in the device since the outer ridge 194 is pushed tightly against the interior wall surface of the outer member 138, and the inner ridge 192 is pushed tightly against the interior ridge 198 on the guide fitting 176.

During use of the blood containment device 130, blood from an accessed blood vessel enters through a distal opening 142 in the rigid inner member 132 from the channel of a vascular entry needle and migrates into the compliant membrane 134. The blood fills up the blood visualization chamber 172 in the compliant membrane 134, and pushes air through the vent opening 164. The air passes through the gas permeable ring 136 and exits the containment device 130 by way of the vent holes 180, 182.

Once the air has escaped, the blood will enter the vent opening 164 and pass into the blood collecting channel 196, forming a pool of blood therein between the inner and outer ridges 192, 194. The pool of blood remains in place because of the seals formed by the inner and outer ridges 192, 194. In addition, when the pool of blood contacts the gas permeable ring 136 made from a self-sealing material, the pool of blood uniformly seals the gas permeable ring 136 against air or blood passing therethrough. The pool of blood thus also aids in providing improved sealing of the containment device 130 to prevent leakage of blood therefrom.

Figure 13:
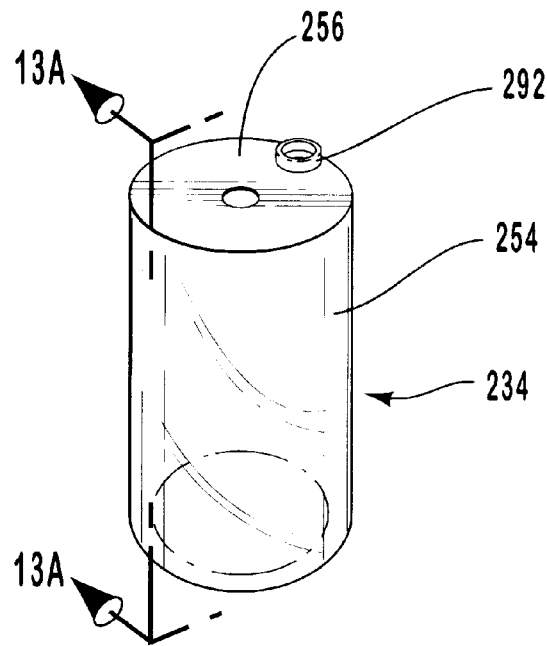
FIG. 13 is a perspective view of an alternative embodiment of the compliant membrane which can be employed in the device of FIG. 9.
Figure 13A:
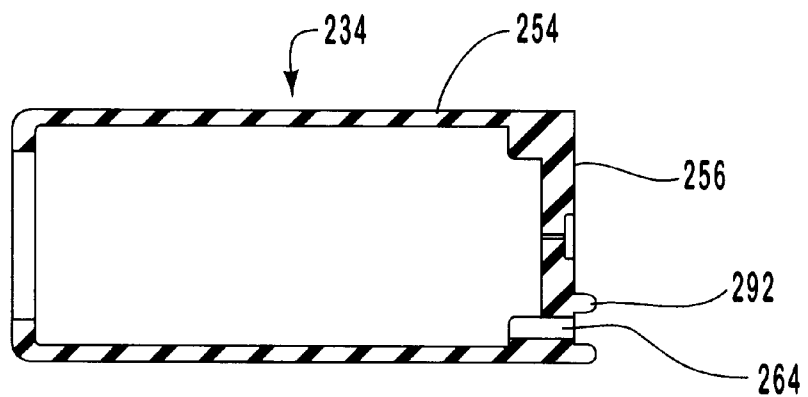
FIG. 13A is a longitudinal cross-sectional view of the compliant membrane of FIG. 13, taken along line 13A—13A of FIG. 13.

It will be appreciated that the sealing means employed in the blood containment device of the invention can be implemented using various other alternative structures and be within the intended scope of the invention. For example, another embodiment of the compliant membrane that can be used in the blood containment device is shown in FIGS. 13 and 13A in the form of a compliant membrane 234. The compliant membrane 234 has a side wall 254 and an end wall 256, with a vent opening 264 formed in the end wall 256. A sealing means to prevent leakage of fluid such as blood is provided on the compliant membrane 234 in the form of a sealing member 292. The sealing member 292 is a protruding circular member, or "stove pipe", formed on the outer surface of the end wall 256 and surrounds the vent opening 264 in the compliant membrane 234.

From the foregoing, it can be seen that a blood containment device for use with a vascular entry needle is provided which fully meets the objects of the instant invention. By the present invention, it is possible to determine by visual and/or tactile indications that an attached vascular entry needle has entered a selected blood vessel and remains properly positioned within the blood vessel. Moreover, the blood is safely contained within the device, preventing significant escape of blood and the attendant contamination risks. An elongated medical instrument, such as a guide wire or catheter, can then be inserted through the device and into the selected blood vessel while blood is contained in the device.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A flexible blood containment member for use in a blood containment device, the flexible blood containment member comprising:

a compliant membrane defining a blood containment chamber into which blood can flow when the blood containment device is placed in fluid communication with a blood vessel;

a vent passage passing through a wall of the compliant membrane and disposed adjacent a gas permeable member of the blood containment device for venting air from the blood containment chamber through the gas permeable member as blood enters the blood containment chamber; and raised sealing means, disposed on an outer surface of the wall of the compliant membrane in abutting contact with the gas permeable member, for preventing significant leakage of blood from the blood containment device.

2. A flexible blood containment member as defined in claim 1, wherein the compliant membrane is significantly transparent such that the blood entering the blood containment chamber is significantly visible.

3. A flexible blood containment member as defined in claim 1, further including a barrier disposed within the wall of the compliant membrane which prevents substantial passage of blood through the barrier but which allows passage of an elongated medical instrument through the barrier.

4. A flexible blood containment member as defined in claim 3, wherein the barrier communicates with a central guideway of the blood containment device passing through at least a portion of the blood containment chamber.

5. A flexible blood containment member as defined in claim 1, wherein the raised sealing means comprises a ridge defining a blood collection channel on one side in communication with the vent passage.

6. A flexible blood containment member as defined in claim 1, wherein the raised sealing means comprises a pair of spaced apart ridges defining a blood collection channel between the pair of ridges in communication with the vent passage.

7. A flexible blood containment member as defined in claim 1, wherein the raised sealing means comprises a pair of spaced apart continuous concentric ridges defining a blood collection channel therebetween in communication with the vent passage.

8. A flexible blood containment member as defined in claim 7, wherein the spaced apart continuous concentric ridges are substantially circular.

9. A flexible blood containment member as defined in claim 1, wherein the compliant membrane is configured such that it is able to move responsively to changes in blood pressure in order to provide continuous tactile confirmation that a blood vessel has been properly accessed.

10. A flexible blood containment member as defined in claim 9, wherein the compliant membrane is substantially translucent in order to provide visual confirmation that a blood vessel has been accessed.

11. A blood containment device for use with a vascular entry needle comprising:

a main body portion including a proximal opening, a distal opening, and a guideway extending therebetween, the distal opening being adapted to communicatively connect to a vascular entry needle, the proximal opening being adapted to receive an elongated medical instrument for passage through the guideway and into the vascular entry needle;

a compliant member disposed around at least a portion of the guideway and defining a blood collection chamber in fluid communication with the distal opening such that blood entering the distal opening is allowed to enter the blood collection chamber;

a vent passage disposed in a wall of the compliant member for allowing the escape of air from the blood collection chamber as blood enters therein;

a gas permeable member in communication with the vent passage which allows air to pass through the gas permeable member but which substantially blocks the passage of blood therethrough; and sealing means, disposed on an outer surface of the wall of the compliant member and in abutting contact with the gas permeable membrane, for preventing substantial leakage of blood from the blood containment device which may pass through the vent passage.

12. A blood containment device as defined in claim 11, wherein the compliant member further includes a substantially liquid-tight barrier disposed within the wall of the compliant member which prevents substantially passage of blood through the barrier but which allows for the passage of an elongated medical instrument therethrough.

13. A blood containment device as defined in claim 11, wherein the gas permeable member comprises a self-sealing material that seals upon contact with blood.

14. A blood containment device as defined in claim 11, wherein the sealing means comprises a raised sealing member.

15. A blood containment device as defined in claim 11, wherein the sealing means comprises a pair of concentric circular ridges defining a blood collecting channel therebetween in communication with the vent passage.

16. A blood containment device as defined in claim 11, wherein the main body portion further includes a guide fitting at a proximal end defining the proximal opening, wherein the guide fitting includes a continuous interior ridge that cooperates with the sealing means to prevent substantial passage of blood from the vent hole to the proximal opening.

17. A blood containment device as defined in claim 16, wherein the sealing means includes a ridge that abuts the continuous interior ridge of the guide fitting.

18. A blood containment device for use with a vascular entry needle comprising:

a main body portion including a proximal opening, a distal opening, and a guideway extending therebetween, the distal opening being adapted to communicatively connect to a vascular entry needle, the proximal opening being adapted to receive an elongated medical instrument for passage through the guideway and into the vascular entry needle;

a compliant member disposed around at least a portion of the guideway and defining a blood collection chamber in fluid communication with the distal opening such that blood entering the distal opening is allowed to enter the blood collection chamber, wherein the compliant member is able to pulsate responsively to changes in blood pressure in order to provide continuous tactile confirmation that a blood vessel has been properly accessed;

a vent opening disposed in a wall of the compliant member which allows air within the blood collection chamber to escape as blood enters the blood collection chamber;

a gas permeable membrane in communication with the vent opening which is substantially permeable to air but which is substantially impermeable to blood; and at least one sealing ridge disposed on an outer surface of the wall of the compliant membrane and in abutting contact with the gas permeable membrane, the at least one sealing ridge defining a blood collection channel in communication with the vent opening.

19. A blood containment device as defined in claim 18, wherein the blood containment device includes a pair of substantially concentric circular sealing ridges that define the blood collection channel therebetween.

20. A blood containment device as defined in claim 18, wherein the compliant member further includes a substantially liquid-tight barrier disposed within the wall of the compliant member which prevents substantially passage of blood through the barrier but which allows for the passage of an elongated medical instrument therethrough, the barrier communicating with the guideway in a way that minimizes the possibility of blood passing from the blood containment chamber through the barrier upon inserting an elongated medical instrument through the barrier.

* * * * *

UNITED STATES PATENT AND TRADEMARK OFFICE
CERTIFICATE OF CORRECTION

PATENT NO. : 5,984,895
DATED : November 16, 1999
INVENTOR(S) : William Padilla, Arlin Dale Nelson It is certified that error appears in the above-identified patent and that said Letters Patent is hereby corrected as shown below:

Col. 11, ln. 52: after "FIG." and before "the rigid" change "1," to --11,--

Signed and Sealed this

Nineteenth Day of December, 2000

Attest:

Q. TODD DICKINSON

*Attesting Officer*   *Commissioner of Patents and Trademarks*